US009504673B2

(12) United States Patent
Nebolsin et al.

(10) Patent No.: US 9,504,673 B2
(45) Date of Patent: Nov. 29, 2016

(54) AGENT FOR THE PROPHYLAXIS AND TREATMENT OF HIGHLY PATHOGENIC INFECTIOUS DISEASES

(75) Inventors: Vladimir Evgenievich Nebolsin, Moscow (RU); Galina Alexandrovna Zheltukhina, Moscow (RU); Sergey Vladimirovich Borisevich, Sergiev Posad (RU); Svetlana Yakovlevna Loginova, Sergiev Posad (RU); Alexander Grigorievich Chuchalin, Moscow (RU)

(73) Assignee: LTD "Valenta-Intellekt", Moscow (RU)

( * ) Notice: Subject to any disclaimer, the term of this patent is extended or adjusted under 35 U.S.C. 154(b) by 525 days.

(21) Appl. No.: 13/320,724

(22) PCT Filed: May 10, 2010

(86) PCT No.: PCT/RU2010/000256
§ 371 (c)(1),
(2), (4) Date: Feb. 8, 2012

(87) PCT Pub. No.: WO2010/134851
PCT Pub. Date: Nov. 25, 2010

(65) Prior Publication Data

US 2012/0129908 A1 May 24, 2012

(30) Foreign Application Priority Data

May 21, 2009 (RU) ................................ 2009119263

(51) Int. Cl.
*A61K 31/415* (2006.01)
*A61K 31/4172* (2006.01)
*A61K 38/05* (2006.01)

(52) U.S. Cl.
CPC ........... *A61K 31/4172* (2013.01); *A61K 38/05* (2013.01)

(58) Field of Classification Search
CPC .................................................... A61K 31/417
USPC .......................................................... 514/400
See application file for complete search history.

(56) References Cited

FOREIGN PATENT DOCUMENTS

| | | | |
|---|---|---|---|
| EP | 1020179 | A2 | 7/2000 |
| RU | 2141483 | C1 | 11/1999 |
| RU | 2338552 | C2 | 11/2008 |
| WO | 99/01103 | | 1/1999 |
| WO | WO 2008/036003 | A1 * | 3/2008 |

OTHER PUBLICATIONS

Young "How to cope with severe acute respiratory syndrome," Chang Gung Medical Journal, 2003, vol. 26, No. 7, pp. 468-473.*
Eckburg et al. "Avian influenza in humans: a practical review for Clinicians," Infections in Medicine, 2005, vol. 22, No. 11, pp. 535-542.*
Terrestrial Animal Health Code, 2008 http://www.oie.int/eng/hormes/ mcode/en_chapitre_1.10.4.html.
Maines T.R., Lu X.H., Erb S.M. et al. Avian influenza (H5N1) viruses isolated from humans in Asia in 2004 exhibit increased virulence in mammals // J. Virol.—2005.—vol. 79, n. 18.—p. 11788-11800.
Cheung C.L., Rayner J.M., Smith G.J. et al. Distribution of amantadine-resistant H5N1 avian influenza variants in Asia // J. Infect. Dis.—2006.—vol. 193.—p. 1626-1629.
Hui-Ling Y., Ilyshina N.A., Salomon R. et al. Neuraminidase ingibitor-resistant recombinant A/Vietnam/1203/04 (H5N1) influenza viruses retain their replication efficiency and pathogenicity in vitro and vivo // J. Virol.—2007.—vol. 81.—p. 12418-12426.
Le Q.M., Kiso M., Someya K. et al. Avian flu: isolation of drug-resistant H5N1 virus // Nature.—2005.—vol. 437.—p. 1108.
Revised U.S. Surveillance case definition for severe acute respiratory syndrome (SARS) and update on SARS cases—United States and worldwide, Dec. 2003 // MMWR Wkly Rep.—2003.—vol. 52, N. 49.—p. 1202-1206.
International Search Report for PCT/RU2010/000256 dated Sep. 30, 2010.

* cited by examiner

*Primary Examiner* — Shengjun Wang
(74) *Attorney, Agent, or Firm* — Fitch Even Tabin & Flannery LLP

(57) ABSTRACT

The invention relates to an agent for the treatment and/or prophylaxis of highly pathogenic infectious diseases, such as highly pathogenic influenza A (in particular, subtypes H5 and H7) and severe acute respirator syndrome caused by the genotype IV coronavirus. The agent is in the form of glutaryl histamine or a pharmaceutically acceptable salt thereof. The invention also relates to a pharmaceutical composition based on glutaryl histamine or a pharmaceutically acceptable salt thereof and to a method for the treatment and/or prophylaxis of highly pathogenic infectious diseases.

(I)

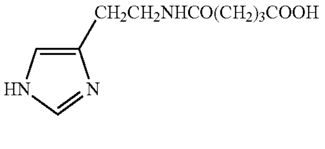

9 Claims, No Drawings

AGENT FOR THE PROPHYLAXIS AND TREATMENT OF HIGHLY PATHOGENIC INFECTIOUS DISEASES

CROSS REFERENCE TO RELATED APPLICATIONS

This application is a national phase application of International Application No. PCT/RU2010/000256, filed May 20, 2010, claiming priority to Russian Application No. 2009119263, filed May 21, 2009, both of which are incorporated by reference herein in their entirety.

TECHNICAL FIELD

The invention relates to glutaryl histamine (GH) of the formula (I)

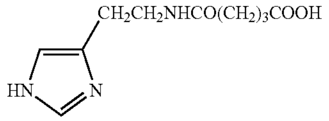

or pharmaceutically acceptable salts thereof as an agent for the treatment and/or prophylaxis of highly pathogenic infectious diseases, such as highly pathogenic influenza A, specifically of subtypes H5 and H7 (hereinafter, highly pathogenic influenza), and severe acute respiratory syndrome (SARS) caused by the genotype IV coronavirus, and also relates to a pharmaceutical composition and a method for the treatment and/or prophylaxis of these diseases.

BACKGROUND ART

According to article 10.4 of the Terrestrial Animal Health Code, highly pathogenic influenza A viruses are those isolates (strains) thereof for which an intravenous pathogenicity index is greater than 1.2 [Terrestrial Animal Health Code, 2008 http://www.oie.int/eng/hormes/mcode/en_chapitre_1.10.4.html].

Another criterion for classifying isolates of influenza A virus strains (for example, H5N1) as highly pathogenic is the dose of this pathogen killing 50% of intranasally infected white mice. Highly pathogenic influenza A virus strains in mice are those having $LD_{50}$ of less than 5.5 lg $EID_{50}$ [Maines, T. R., Lu, X. H., Erb, S. M., et al., “Avian Influenza (H5N1) Viruses Isolated from Humans in Asia in 2004 Exhibit Increased Virulence in Mammals,”//J. Virol, 2005, Vol. 79, No. 18, pp. 11788-11800].

The major tools for the prevention and control of epidemic (pandemic) influenza are chemotherapy, chemoprophylaxis, and vaccination.

In view of the impossibility of predicting the antigenic structure of a future epidemic (pandemic) influenza A virus, the early design of effective influenza vaccines is difficult, and it is therefore important to have in the arsenal chemotherapeutic agents for the prophylaxis and treatment of diseases caused by highly pathogenic virus strains.

Arbidol® is one of the most common medications for the treatment and prophylaxis of viral infections, specifically influenza. In oral administration in vivo tests for emergency prevention and treatment (135 mg/kg body weight in white mice), however, the protective efficacy of Arbidol® against the highly pathogenic influenza A (H5N1) virus strain is as low as 25 and 10%, respectively (see Tables 2 and 3).

This protection level does not meet the existing national requirements for the efficacy of antiviral chemotherapeutics (which should be no less than 30%) [Руководство по экспериментальному (доклиническому) изучению новых фармакологических веществ.—М., 2005.—С. 541 (The Manual on Experimental (Preclinical) Study of Novel Pharmacological Agents, Moscow, 2005, p. 541)].

Adamantane derivatives are also well-known chemotherapeutics, which have been in use in the therapy of seasonal influenza since the 1960s. The recently isolated strains of highly pathogenic influenza A(H5N1) virus had a high-level resistance to adamantane derivatives, namely to amantadine and rimantadine; for this reason, these medications have lost their therapeutic role [Cheung, C. L., Rayner, J. M., Smith, G. J., et al., “Distribution of Amantadine-Resistant H5N1 Avian Influenza Variants in Asia,” J. Infect. Dis., 2006, Vol. 193, pp. 1626-1629].

Neuraminidase inhibitor oseltamivir is the most efficient agent for treating influenza. Many influenza A subtype H5N1 virus strains have recently acquired resistance to oseltamivir due to the replacement of one amino acid in neuraminidase N1 (His274Tyr and N294S) [Hui-Ling, Y., Ilyshina, N. A., Salomon, R., et al. “Neuraminidase Inhibitor-Resistant Recombinant A/Vietnam/1203/04 (H5N1) Influenza Viruses Retain Their Replication Efficacy and Pathogenicity in vitro and vivo,” J. Virol, 2007, Vol. 81, pp. 12418-12426; Le, Q. M., Kiso, M., Someya, K., et al. “Avian Flu: Isolation of Drug-Resistant H5N1 Virus,” Nature, 2005, Vol. 437, p. 1108].

Thus, the medications commonly used against seasonal influenza strains prove to be inefficient against highly pathogenic strains.

One more highly pathogenic viral disease is severe acute respiratory syndrome (SARS), a new acute coronavirus disease which is caused by the genotype IV pathogen and characterized by up to 10% mortality [Revised U.S. Surveillance Case Definition for Severe Acute Respiratory Syndrome (SARS) and Update on SARS Cases, United States and Worldwide, December 2003, MMWR Wkly Rep., 2003, Vol. 52, No. 49, pp. 1202-1206].

Therefore, there is a need in developing new agents for the treatment and/or prophylaxis of highly pathogenic influenza and SARS. The inventors unexpectedly found that glutaryl histamine is useful as such an agent and this resulted in the development of the present invention.

SUMMARY OF THE INVENTION

The invention relates to an agent for the treatment and/or prophylaxis of highly pathogenic infectious diseases, such as highly pathogenic type A influenza, in particular subtypes H5 and H7 (hereinafter, highly pathogenic influenza), and severe acute respiratory syndrome caused by the genotype IV coronavirus, this agent representing glutaryl histamine

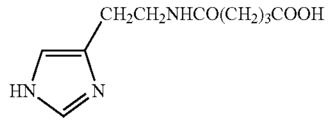

or a pharmaceutically acceptable salt thereof.

Further, provided is a pharmaceutical composition for the treatment and/or prophylaxis of highly pathogenic infectious diseases, comprising an efficient amount of glutaryl histamine or a pharmaceutically acceptable salt thereof in combination with one or more pharmaceutically acceptable carriers.

Still further, the invention relates to a method for the treatment and/or prophylaxis of highly pathogenic infectious diseases, comprising administering to a patient in need thereof an efficient amount of glutaryl histamine or a pharmaceutically acceptable salt thereof.

DETAILED DESCRIPTION OF THE INVENTION

The glutaryl histamine (GH) compound of the formula

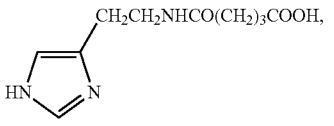

was first described in WO 99/01103, Jan. 14, 1999, where its synthesis was disclosed and where this compound was discovered to have a wide spectrum of biological properties, including antibacterial and antiviral activities. The antiviral activity of glutaryl histamine was studied against the human encephalomyocarditis virus, the influenza A (seasonal) virus, and the HIV-1 virus (see WO 99/01103, Example 44). Noteworthy, neither the HIV virus nor the human encephalomyocarditis vims (picomavirus) relates to highly pathogenic viruses [Terrestrial Animal Health Code, 2008 http://www.oie.int/eng/hormes/mcode/en_chapitre_1.10.4.html]. Seasonal influenza viruses are not classified as highly pathogenic viruses for the reason that they have low intravenous pathogenicity index (lower than 1.2).

The inventors unexpectedly found that glutaryl histamine and pharmaceutically acceptable salts thereof may be efficiently used for the prophylaxis and/or treatment of highly pathogenic viral diseases, such as highly pathogenic influenza A (in particular, subtypes H5 and H7) and severe acute respiratory syndrome (SARS).

Thus, the invention relates to an agent for the treatment and/or prophylaxis of highly pathogenic infectious diseases, which represents glutaryl histamine of the formula

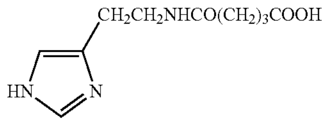

or a pharmaceutically acceptable salt thereof.

More particular, the invention relates to an agent for the treatment and/or prophylaxis of highly pathogenic influenza A (in particular, subtypes H5 and H7), this agent representing glutaryl histamine or a pharmaceutically acceptable salt thereof.

H5N1, H7N2, H7N7, and H9N2 are particular examples of highly pathogenic influenza A subtypes for the treatment and/or prophylaxis of which glutaryl histamine or a pharmaceutically acceptable salt thereof is useful.

In another embodiment, the invention relates to an agent for the treatment and/or prophylaxis of severe acute respiratory syndrome (SARS) caused by the genotype IV coronavirus, this agent representing glutaryl histamine of the formula

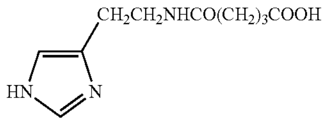

or a pharmaceutically acceptable salt thereof.

Further, the invention relates to a pharmaceutical composition for the treatment and/or prophylaxis of highly pathogenic infectious diseases, comprising an efficient amount of glutaryl histamine or a pharmaceutically acceptable salt thereof as an active ingredient and one or more pharmaceutically acceptable carriers.

In one more embodiment of the invention, the pharmaceutical composition is intended for the treatment and/or prophylaxis of highly pathogenic influenza A, in particular subtypes H5 and H7, more particularly, subtypes H5N1, H7N2, H7N7 and H9N2. In still one more embodiment of the invention, the pharmaceutical composition is intended for the treatment and/or prophylaxis of severe acute respiratory syndrome (SARS) caused by the genotype IV coronavirus.

Further the invention relates to a method for the treatment and/or prophylaxis of highly pathogenic infectious diseases, comprising administering to a patient in need thereof an efficient amount of glutaryl histamine or a pharmaceutically acceptable salt thereof. A patient may be a mammal or a bird. Glutaryl histamine or pharniaceutically acceptable salts thereof may be administered either individually or in the above-described pharmaceutical composition.

In one more embodiment, the invention relates to a method for the treatment and/or prophylaxis of highly pathogenic influenza A, in particular subtypes H5 and H7, more particularly, subtypes H5N1, H7N2, H7N7, and H9N2. In still one more embodiment, the invention relates to a method for the prophylaxis and/or treatment of severe acute respiratory syndrome (SARS) caused by the genotype IV coronavirus.

Further, the invention relates to the use of glutaryl histamine or a pharmaceutically acceptable salt thereof for the treatment and/or prophylaxis of highly pathogenic infectious diseases, such as highly pathogenic type A influenza, in particular subtypes H5 and H7, more particularly, H5N1, H7N2, H7N7, and H9N2, and severe acute respiratory syndrome (SARS) caused by the genotype IV coronavirus.

Pharmaceutically acceptable salts of glutaryl histamine according to the invention may be salts thereof with alkali or alkaline-earth metals, preferably sodium, potassium, and lithium salts.

Glutaryl histamine or salts thereof are administered in an efficient amount to provide the desired therapeutic result.

Glutaryl histamine or salts thereof may be administered to a patient in daily doses of from 0.1 to 100 mg/kg of the body weight of the mammal, preferably in doses of from 0.3 to 30 mg/kg, one or more times a day.

It must be noted that a particular dose for a particular patient will depend on many factors, such as patient's age, body weight, gender, general health condition, and diet; the schedule and route of administrating the agent and its excretion rate from the body; and the severity of disease in the individual under treatment.

The pharmaceutical compositions of the invention comprise GH or a pharmaceutically acceptable salt thereof in an amount efficient for providing the desired result, and may be prepared as unit dosage forms (for example, in solid, semi-solid, or liquid forms) that comprise GH or a salt thereof as an active ingredient in a mixture with a carrier or an excipient suitable for intramuscular, intravenous, oral, sublingual, inhalation, intranasal, rectal, and transdermal administration. The active ingredient may be included into the composition together with conventional nontoxic pharmaceutically acceptable carriers suitable for manufacturing solutions, tablets, pills, capsules, dragee, suppositories, emulsions, suspensions, ointments, gels, patches, and any other dosage forms.

Diverse excipients may be used, such as glucose, lactose, of sucrose; marmitoi or sorbitol; cellulose derivatives; and/or calcium phosphates, for example, tricalcium phosphate or calcium hydro-phosphate. The following binders may be used: starch paste (for example, corn, wheat, rice, or potato starch), gelatin, tragacanth, methylcellulose, hydroxypropylmethylcellulose, sodium carboxymethylcellulose, and/or polyvinylpyrrolidone. If needed, disintegrating agents may be used, such as the aforementioned starches and carboxymethylstarch, crosslinked polyvinylpyrrolidone, agar-agar, or alginic acid or a salt thereof, such as sodium alginate.

Optional additives may be used, such as flowability control agents and lubricating agents, such as silica, talc, stearic acid and salts thereof, such as magnesium stearate or calcium stearate, and/or propylene glycol.

Stabilizing, thickening, colorant, and fragrance additives may also be used.

The ointment base may be a hydrocarbon ointment base, such as white Vaseline and yellow Vaseline (Vaselinum album and Vaselinum flavum, respectively), Vaseline oil (Oleum Vaselini), and white ointment and liquid ointment (Unguentum album and Unguentum flavum, respectively). Useful thickening additives are such as solid paraffin and wax; absorptive ointment bases, such as hydrophilic Vaseline (Vaselinum hydrophylicum), lanoline (Lanolinum), and cold cream (Unguentum leniens); water-removable ointment bases, such as hydrophilic ointment (Unguentum hydrophylum); and water-soluble ointment bases, such as polyethylene glycol ointment (Unguentum Glycolis Polyaethyleni); bentonite bases; and others.

As bases for gels, useful are methylcellulose, sodium caboxymethylcellulose, oxypropylcellulose, polyethylene glycol or polyethylene oxide, and carbopol.

As bases for suppositories, useful are water-insoluble bases such as cocoa butter; water-soluble or water-miscible bases, such as gelatin-glycerol or polyethylene oxide bases; and combination (soap-glycerol) bases.

In preparing a unit dosage form, the amount of an active ingredient used in combination with a carrier may vary depending on the recipient of the therapy and on the route in which the therapeutic agent is administered.

For example, when GH or a salt thereof is used in the form of solutions for injection, the active agent in this solution is in an amount of 0.1 to 5%. As diluents, 0.9% sodium chloride solution, distilled water, Novocaine solution for injections, Ringer solution, glucose solution, and specific solubilizing adjuvants may be used. When GH or a salt thereof is administered in the form of tablets or suppositories, its amount is 10 to 300 mg per unit dosage form.

The dosage forms of the invention are manufactured by routine procedures, such as blending, granulation, forming dragee, dissolution, and lyophilization.

It is pertinent that doses in which GH or salts thereof are biologically active are one order of magnitude lower than for the prior-art analogues with practically equal or higher efficacies, and no adverse side effects have been found for GH.

Below the invention will be described in a detailed way be means of examples, which are intended to illustrate the preferred embodiments of the invention and in no means limit the scope thereof.

Example 1

Acute Toxicity Study of Glutaryl Histamine

The acute toxicity of glutaryl histamine was studied in nonlinear white male mice with body weights of 28 to 30 g. For intragastric administration, $LD_{50}$ was found to be greater than 10 000 mg/kg.

Example 2

Prophylactic and Therapeutic Efficacy of Glutaryl Histamine against H5N1 Influenza Virus The antiviral activity of the medicaments used was studied subject to the requirements recited in the appropriate manual [Руководство по экспериментальному (доклиничсскому) изучению новых фармакологических веществ. —M., 2005—C. 532-545 (The Manual on Experimental (Preclinical) Study of Novel Pharmacological Agents, Moscow, 2005, pp. 532-545)].

The prophylactic and therapeutic efficacy against the A/chicken/Kurgan/Russia/2/05 (H5N1) influenza virus strain was ascertained in vivo in white mice having body weights of 10 to 12 g. The infective agent used was the allantoic fluid from infected DCE (developing chick embryos) having biological activity values of 6.5 lg $CPD_{50}$/ml, 9.0 lg $ELD_{50}$/ml, and 5.0 lg $LD_{50}$/ml.

Glutaryl histamine was administered to white mice orally for emergency prevention and for treatment.

Table 1 shaws the results obtained for the prophylactic efficacy of the agent against induced highly pathogenic influenza in white mice that have been intranasally infected with the A/chicken/Kurgan/Russia/02/05 (H5N1) influenza strain.

Table 1 makes it clear that the percent protection from death with the use of the agent of the invention averages 45.0%, providing clear evidence of the prophylactic efficacy of glutaryl histamine.

Tables 2 and 3 display the results obtained in studying GH efficacy in emergency prevention and therapeutic uses, respectively.

TABLE 1

Prophylactic efficacy of GH against induced influenza in white mice intranasally infected with the influenza virus strain A/chicken/Kurgan/Russia/02/05 (H5N1)

| Agent | Administration schedule | Dose, mg/kg | Number of animals in the group | Deaths | Protective efficacy against death, % | Mean lifetime of animals in the group, days | Increase of mean lifetime Δ, days |
|---|---|---|---|---|---|---|---|
| Compound of the formula I (GH) | −120 h, −96 h, −72 h, −48 h, −24 h, −1 h | 5.0 | 20 | 11 | 45 | 10.9 | 2.7 |

TABLE 1-continued

Prophylactic efficacy of GH against induced influenza in white mice intranasally
infected with the influenza virus strain A/chicken/Kurgan/Russia/02/05 (H5N1)

| Agent | Administration schedule | Dose, mg/kg | Number of animals in the group | Deaths | Protective efficacy against death, % | Mean lifetime of animals in the group, days | Increase of mean lifetime Δ, days |
|---|---|---|---|---|---|---|---|
| Infected untreated control | — | — | 20 | 20 | — | 8.2 | — |
| Uninfected control | — | — | 20 | 0 | — | 14 | — |

TABLE 2

Efficacy of GH in emergency prevention of induced influenza in white mice intranasally
infected with the influenza virus strain A/chicken/Kurgan/Russia/02/05 (H5N1)

| Agent | Administration schedule | Dose, mg/kg | Death rate | Protective efficacy against death, % | Mean lifetime of animals in the group, days | Increase of mean lifetime Δ, days |
|---|---|---|---|---|---|---|
| Compound of the formula (I) (GH) | +1 h, +24 h, +48 h, +72 h, +96 h, +120 h, 144 h | 5.0 | 12/20 | 40 | 10.0 | 1.8 |
|  |  | 15.0 | 12/20 | 40 | 11.0 | 2.4 |
| Arbidol ® |  | 135.0 | 15/20 | 25 | 8.0 | 1.4 |
| Infected untreated control | — | — | 20/20 | — | 8.2 | — |
| Uninfected control | — | — | 0/20 | — | 14.0 | — |

TABLE 3

Therapeutic efficacy of GH against induced influenza in white mice intranasally infected
with the influenza virus strain A/chicken/Kurgan/Russia/02/05 (H5N1)

| Agent | Administration schedule | Dose, mg/kg | Death rate | Protective efficacy against death, % | Mean lifetime of animals in the group, days | Increase of mean lifetime Δ, days |
|---|---|---|---|---|---|---|
| Compound of the formula (I), (GH) | +24 h, +48 h, +72 h, +96 h, +120 h, +144 h | 15 | 13/20 | 35 | 8.7 | 2.0 |
| Arbidol ® |  | 135.0 | 18/20 | 10 | 7.2 | 1.1 |
| Infected untreated control | — | — | 20/20 | — | 6.7 | — |
| Uninfected control | — | — | 0/20 | — | 14.0 | — |

The experimental data compiled in Tables 2 and 3 provide clear evidence of the efficacy of glutaryl histamine both for treatment and for emergency prevention.

Example 3

Efficacy Against the Severe Acute Respiratory Syndrome Pathogen

For assessment of prophylactic and therapeutic efficacy, Syrian hamsters were infected with the severe acute respiratory syndrome virus orally in a dose of $1 \times 10^5$ PFU. Glutaryl histamine was administered orally in doses of 5.0 and 15.0 mg/kg in the following schedules: for prophylaxis, once daily pre-virus exposure for 7 days and 1 h pre-virus exposure; for treatment, beginning 24 h post-virus exposure and further for 6 days.

The results of the efficacy studies are found in Table 4.

TABLE 4

Efficacy of glutaryl histamine against induced severe acute respiratory syndrome in Syrian hamsters

| Agent | Dose, mg/kg | Schedule | Therapeutic efficacy, % | Virus yield in the lungs at peak of infection (on day 4) | |
|---|---|---|---|---|---|
|  |  |  |  | 1 g PFU/ml | Δ, 1 g |
| Compound of the formula (I) (GH) | 5 | −144 h, −120 h, −96 h, −72 h, −48 h, −24 h, −1 h | 30.0 | 7.0 | 0.9 |

TABLE 4-continued

Efficacy of glutaryl histamine against induced severe acute respiratory syndrome in Syrian hamsters

| Agent | Dose, mg/kg | Schedule | Therapeutic efficacy, % | Virus yield in the lungs at peak of infection (on day 4) 1 g PFU/ml | Δ, 1 g |
|---|---|---|---|---|---|
| | 15 | +24 h, +48 h, +72 h, +96 h, | 40.0 | 3.8 | 2.4 |
| | 5 | +120 h, +144 h | 20.0 | 7.5 | 0.8 |
| Infected untreated control | | — | — | 8.3 | — |
| Uninfected control | | — | — | — | — |

The data displayed in this table provide evidence that the claimed compound is efficient against induced SARS in Syrian hamsters. The therapeutic efficacy of the agent administered in a dose of 15 mg/kg for treatment was 40%; and in a dose of 5 mg/kg for prevention and treatment, the efficacy was 30% and 20% of the infected animals, respectively.

These results imply that the claimed compound may find use in the treatment of various highly pathogenic infectious diseases.

Example 4

Unit Dosage Forms Based on Glutaryl Histamine

A. Gelatin capsules.

Glutaryl histamine or a salt thereof: 90 mg; and

Lactose (milk sugar), potato starch, colloidal silica (Aerosil), and magnesium stearate, to bring the weight contents of the capsule to 220 mg.

The aforementioned ingredients are mixed and granulated; the granules are placed in hard gelatin capsules in an amount of 220 mg.

B. Solution for injections

The solvents useful to prepare solutions for injection are 0.9% sodium chloride solution, distilled water, or Novocaine solution. Unit dosage forms may be manufactured as ampoules, vials, ampins, and inserts.

The formulation of the solution for injection is as follows:

Glutaryl histamine or a salt thereof: 100 mg; and

Distilled water: 5 ml.

Injection dosage forms may be manufactured as sterile solutions, sterile powders, and sterile tablets.

The invention claimed is:

1. A method for the treatment of highly pathogenic infectious diseases, comprising administering to a patient in need thereof an effective amount of glutaryl histamine of the formula

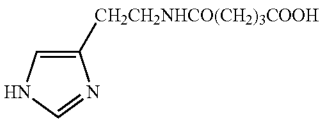

or a pharmaceutically acceptable salt thereof, wherein the highly pathogenic infectious diseases is highly pathogenic influenza A of subtype H5 and/or severe acute respiratory syndrome (SARS) caused by genotype IV coronavirus.

2. The method according to claim 1, wherein highly pathogenic influenza A is of subtype H5N1.

3. The method according to claim 1, wherein glutaryl histamine or a pharmaceutically acceptable salt thereof is administered individually or in a pharmaceutical composition.

4. The method according to claim 2, wherein glutaryl histamine or a pharmaceutically acceptable salt thereof is administered individually or in a pharmaceutical composition.

5. A method for increasing a rate of survival of highly pathogenic influenza A virus infection of subtype H5, the method comprising administering to a patient in need thereof an effective amount of glutaryl histamine of the formula

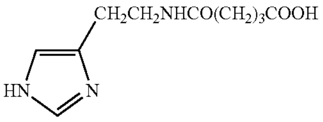

or a pharmaceutically acceptable salt thereof prior to exposure to highly pathogenic influenza A virus of subtype H5.

6. The method according to claim 5, wherein highly pathogenic influenza A is of subtype H5N1.

7. The method according to claim 5, wherein glutaryl histamine or a pharmaceutically acceptable salt thereof is administered individually or in a pharmaceutical composition.

8. The method according to claim 6, wherein glutaryl histamine or a pharmaceutically acceptable salt thereof is administered individually or in a pharmaceutical composition.

9. A method for decreasing virus yield in the lungs of a subject having severe acute respiratory syndrome (SARS) caused by genotype IV coronavirus, the method comprising administering to the subject an effective amount of glutaryl histamine of the formula

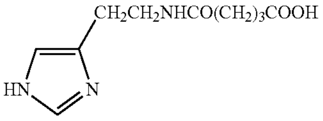

or a pharmaceutically acceptable salt thereof prior to exposure to genotype IV coronavirus.

* * * * *

UNITED STATES PATENT AND TRADEMARK OFFICE

CERTIFICATE OF CORRECTION

PATENT NO. : 9,504,673 B2
APPLICATION NO. : 13/320724
DATED : November 29, 2016
INVENTOR(S) : Nebolsin et al.

It is certified that error appears in the above-identified patent and that said Letters Patent is hereby corrected as shown below:

On the Title Page

Under “(22) PCT Filed,” delete “May 10, 2010” and insert --May 20, 2010-- therefor.

In the Claims

Column 3, Line 30, delete “vims (picomavirus)” and insert --virus (picornavirus)-- therefor.

Column 4, Line 28, delete “pharniaceutically” and insert --pharmaceutically-- therefor.

Column 5, Line 8, delete “marmitoi” and insert --mannitol-- therefor.

Column 5, Line 10, delete “hydro-phosphate” and insert --hydrophosphate-- therefor.

Column 6, Line 43, delete “shaws” and insert --shows-- therefor.

Signed and Sealed this
Fourth Day of August, 2020

Andrei Iancu
*Director of the United States Patent and Trademark Office*